United States Patent [19]

Marshall

[11] Patent Number: 4,830,010

[45] Date of Patent: May 16, 1989

[54] METHODS FOR THE DIAGNOSIS OF GASTROINTESTINAL DISORDERS

[76] Inventor: Barry J. Marshall, 25 Bondi Street, Mount Hawthorn 6016, Perth, Western Australia, Australia

[21] Appl. No.: 147,058

[22] Filed: Jan. 22, 1988

Related U.S. Application Data

[63] Continuation of Ser. No. 848,413, Apr. 4, 1986, abandoned.

[51] Int. Cl.$^4$ ................................................. A61B 5/00
[52] U.S. Cl. ..................................... 128/630; 128/719; 436/811; 424/9
[58] Field of Search ....................... 128/630, 659, 719; 424/1.1, 9; 436/804, 811; 356/51

[56] References Cited

U.S. PATENT DOCUMENTS 4,548,805 10/1985 Sack et al. ............................... 424/9

OTHER PUBLICATIONS

"Evaluation of the Breath Test in the Detection of Bacterial Colonisation of the Upper Gastrointestinal Tract", *The Lancet*, Parkin et al., Oct. 14, 1972, pp. 777–780.

"The Cholyl Glycine-1-$^{14}$C Breath Test in Various Gastrointestinal Disorders", *Digestion* 19, Peled et al., 1979, pp. 267–276.

"Pharmacokinetics of Acetohydroxamic Acid in Patients with Staghorn Renal Calculi", *European Journal of Clinical Pharmacology*, Putcha et al., 1985, pp. 439–445.

"C—14 and C—13 Carbon Dioxide Tests: Measurement of G. I. Function" by Spitznagle, *Interventional Nuclear Medicine*, 1984, pp. 321–334.

Kornberg et al, "The Breakdown of Urea in Cats not Secreting Gastric Juice", *Biochem. J.*, 56, pp. 355–363 (1954).

Kornberg et al, "The Activity and Function of Gastric Urease in the Cat", *Biochem. J.*, 56, pp. 363–372 (1954).

Kornberg et al, "Gastric Urease", *Physio. Rev.*, 35, pp. 169–177 (1955).

Dintzis et al, "The Effect of Antibiotics on Urea Breakdown in Mice", *Proceedings of the National Academy of Sciences*, 39, pp. 571–578 (1953).

Marshall et al, "Attempt to Fulfill Koch's Postulates for Pyloric Campylobacter", *The Medical Journal of Australia*, 142, pp. 436–439 (1985).

Piper, "Bacteria, Gastritis, Acid Hyposecretion and Peptic Ulcer", *The Medical Journal of Australia*, 142, p. 431 (1985).

P. D. Klein et al., "The Commercial Feasibility of $^{13}$C Breath Tests", 11 Analytical Chemistry Symposium Series 347–352 (1982).

B. J. Marshall et al., "Unidentified Curved Bacilli in the Stomach of Patients with Gastritis & Peptic Ulceration", 1 Lancet 1311–1315 (1984).

M. L. Langenberg et al., "Campylobacter-like Organisms in the Stomach of Patients & Healthy Individuals", 1 Lancet 1348 (1984).

P. D. Klein et al., "Stable Isotopes and Mass Spectrometry in Nutrition Science", 21 Analytical Chemistry Symposium Series 155–166 (1984).

B. J. Marshall et al., "Pyloric Campylobacter Infection and Duodenal Disease", 142 Medical J. of Australia 439–444 (1985).

C. A. M. McNulty et al., "Rapid Diagnosis of Campylobacter-Associated Gastritis", 1 Lancet 1443–1444 (1985).

B. J. Marshall, "Perspective-Campylobacter Pyloridic and Gastritis", 153, J. of Infectious Diseases 650–657 (1986).

*Primary Examiner*—Edward M. Coven
*Assistant Examiner*—Randy Citrin
*Attorney, Agent, or Firm*—David L. Suter; Kim W. Zerby; Richard C. Witte

[57] ABSTRACT

Methods for the diagnosis of gastrointestinal disorders in human or lower animal subjects comprising the steps of administering to said subject a safe and effective amount of urea and analyzing the breath of said subject for the presence of carbon dioxide or ammonia products of the hydrolysis of said urea, wherein the presence of said hydrolysis products is a positive indication of a gastrointestinal disorder in said subject. Preferably the administered urea contains isotope-labelled nitrogen or carbon.

7 Claims, No Drawings

4,830,010

METHODS FOR THE DIAGNOSIS OF GASTROINTESTINAL DISORDERS

This is a continuation of application Ser. No. 848,413, filed on Apr. 4, 1986, now abandoned.

BACKGROUND OF THE INVENTION

This invention relates to methods for the diagnosis of gastrointestinal disorders in humans and other animals.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract is generally defined as including the esophagus, the stomach, the duodenum, the jejunum, and ileum.) Peptic ulcers are lesions of the gastrointestinal tract lining, characterized by loss of tissue due to the action of digestive acids and pepsin. It has been generally held that peptic ulcers are caused by gastric hypersecretion, decreased resistance of the gastric lining to digestive acids and pepsin or both. Gastritis is, by definition, an inflammation of the stomach mucosa. In practice, though, the disorder is manifested by a broad range of poorly-defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, 1311–1315 (1984), and in R. Greenlaw, et al., "Gastroduodenitis, A Broader Concept of Peptic Ulcer Disease", 25 *Digestive Diseases and Sciences* 660–672 (1980).

As with the management of any disorder, the rapid, precise, and accurate diagnosis of gastrointestinal disorders is of paramount importance. The typical means used to diagnose the gastrointestinal disorder presented by a given patient will depend upon such factors as the nature and severity of symptoms, the overall health of the individual, the medical history of the patient, the need for a specific diagnosis in order to implement a treatment with reasonable likelihood of success, and the availability of diagnostic devices. However, the diagnostic methods typically employed in the art are often slow, cumbersome, costly and may yield equivocal or inaccurate results. See, e.g., Spiro, supra. Thus, for patients not having severe symptoms, a precise diagnosis of a gastrointestinal disorder might not be attempted. Such patients may simply be treated with conventional therapies, such as with antacids or drugs which inhibit stomach acid secretion. While such therapies might provide temporal symptomatic relief, a "cure" is often not effected. See, for example, A. J. McLean, et al., "Cytoprotective Agents and Ulcer Relapse", 142 *The Medical Journal of Australia*, Special Supplement, S25–S28 (1985), and O. Nyren, et al., "Absence of Therapeutic Benefit from Antacids or Cimetidine in Non-ulcer Dyspepsia" 314 *New England Journal of Medicine* 339–343 (1986). More effective treatments may depend upon better diagnoses of the actual underlying gastrointestinal disorder. In particular, it has been discovered that many such gastrointestinal disorders are mediated by infection of gastric mucosa by bacteria. See, B. J. Marshall, et al, "Pyloric Campylobacter Infection and Gastroduodenal Disease," the *Medical Journal of Australia*, 439–444 (1985). Thus, treatment of the bacterial infection may be required in order to effectively treat the manifested gastrointestinal disorder.

Accordingly, a simple diagnostic test for gastrointestinal disorders could afford substantial advantages in the proper and effective treatment of patients having gastrointestinal disorders. Such a test should be easily performed, allowing definitive interpretation, and yield a result with a high degree of correlation to the presence or absence of the gastrointestinal disorder. A blood serum test for gastritis is suggested, for example, in B. J. Marshall, et al., "Pyloric Campylobacter Serology", 2, *The Lancet*, 1442 (1985). A blood serum test for pepsinogen is described in I. M. Samloff, et al., "Relationships Among Serum Pepsinogen I, Serum Pepsinogen II and Gastric Mucosal Histology." 83 *Gastroenterology* 204–209 (1982). A non-invasive test for gastric acid activity is described in U.S. Pat. No. 4,548,805, Sack, et al., issued Oct. 22, 1985.

It has now been discovered that gastrointestinal disorders of the upper gastrointestinal tract may be detected and diagnosed by methods involving the administration to a human or lower animal subject of urea followed by analyzing the breath of the subject to detect the presence of products of urea hydrolysis. The methods of this invention thus provide a rapid, inexpensive, non-invasive and accurate diagnosis of such gastrointestinal disorders.

SUMMARY OF THE INVENTION

The present invention provides methods for the diagnosis of gastrointestinal disorders in human or lower animal subjects. These methods comprise the steps of administering to said subject a safe and effective amount of urea and analyzing the breath of said subject for the presence of carbon dioxide or ammonia products of the hydrolysis of said urea, wherein the presence of said hydrolysis products is a positive indication of a gastrointestinal disorder in said subject. In a preferred method of this invention, carbon atoms in the urea are isotope-labelled, i.e., having a substantial portion of carbon-13 or carbon-14 isotopes in the urea molecule. The breath of the test subject is then analyzed for the presence of isotope-labelled carbon dioxide.

DESCRIPTION OF THE INVENTION

The present invention provides methods for the diagnosis of gastrointestinal disorders in a human or lower animal subject, comprising the steps of administering to said subject a safe and effective amount of urea and analyzing the breath of said subject for the presence of carbon dioxide or ammonia products of hydrolysis of said urea. The presence of said products of hydrolysis is a positive indication of a gastrointestinal disorder in the test subject.

As used herein, "gastrointestinal disorder" encompasses any disease or other disorder of the gastrointestinal tract of a human or lower animal. Such gastrointestinal disorders include, for example: disorders not manifested by presence of ulcerations in the gastric mucosa (herein "non-ulcerative gastrointestinal disorder"), including chronic or atrophic gastritis, gastroenteritis, non-ulcer dyspepsia, esophogeal reflux disease and gastric motility disorders; and "peptic ulcer disease", i.e., gastric and duodenal ulcers. In particular, "gastrointestinal disorder" refers to such disorders of the upper gastrointestinal tract caused or mediated by bacteria, including *Campylobacter pyloridis*. Such Campylobacter include those described in J. R. Warren and B. J. Marshall, "Unidentified Curved Bacilli on Gastric Epithelium in Active Chronic Gastritis", *The Lancet* 1273–1275 (1983), incorporated by reference herein.

Administration of Urea

A first step of the methods of this invention involves administration to a human or lower animal subject of a safe and effective amount of urea, typically from about 1 mg to about 20 mg of urea per kilogram body weight of said subject. As used herein, the term "safe and effective amount" refers to an amount of urea which is sufficient to produce a detectable level of carbon-dioxide or ammonia, without undue adverse side effects (such as toxicity, irritation or allergic responses) commensurate with a reasonable risk/benefit ratio. The specific safe and effective amount of urea to be administered may depend upon such factors as the particular breath analysis method to be used, the weight of the test subject, and (when using isotope-labelled urea) the relative amount or concentration of isotope present in the urea.

Urea, or carbonyldioxide, is of the formula $H_2NCONH_2$, and is a naturally occurring product of protein metabolism. Urea for use in the compositions of this invention is available from a variety commercial sources. As a basis for this invention, it has been found that gastric materials from humans or other animals having gastrointestinal disorders contain relatively large quantities of urease (urea amidohydrolase), which hydrolizes urea to ammonium carbonate, or ammonia and carbon dioxide. The methods of this invention serve, in part, to detect the presence of urease through its hydrolysis of urea.

As used herein, the terms "administering" or "administration of" urea refer to any method in accordance with good medical practice of introducing urea into the stomach of the test subject. Such administration is preferably by oral ingestion of urea, in single or multiple doses. The particular dosage form used to administer the urea may be, for example, in solid tablets or capsules, or in liquid solutions or emulsions. The urea may be administered essentially in pure form, or as part of a composition. Compositions useful in administration of urea may also contain pharmaceutically-acceptable components such as, for example, diluents, emulsifiers, binders, lubricants, glydants, colorants, flavors and sweeteners. Such optional components are among those described in *The Theory and Practice of Industrial Pharmacy*, (L. Lachman, et al., ed. 1976), incorporated by reference herein. Optional components useful herein must not, however, interfere with hydrolysis of the urea, or generate appreciable quantities of carbon dioxide or ammonia in the stomach. A preferred optional component is one which delays gastric emptying, thereby increasing the length of time that the administered urea is present in the stomach.

In a given quantity of naturally occurring urea, the distribution of the various isotopes of carbon and nitrogen comprising the urea molecules is essentially identical to the broad distribution of those isotopes in nature. Accordingly, for example, the carbon atoms in a given sample of urea are predominantly carbon-12, with small quantities of carbon-13 (approximately 1.1%). Carbon-14 isotope, which is a radioactive, unstable isotope with a half-life of approximately 5730 years, is generated by neutron bombardment of carbon-13. (Production of carbon-14 occurs naturally in the upper atmosphere. Carbon-14 enriched compounds are also available as a product of fission reactors.) Nitrogen atoms are predominantly nitrogen-14, with trace quantities (approximately 0.4%) of nitrogen-15 isotope. However, depending upon the intended method to be employed in the analyzing step of this invention, it may be desired to administer isotope-labelled urea, to facilitate detection of isotope-labelled carbon dioxide or ammonia generated by hydrolysis of urea in the stomach of the test subject. As used herein, the term "isotope-labelled" refers to a compound (urea or its hydrolysis products) having a distribution of carbon and/or nitrogen isotopes significantly different from the distribution of carbon and/or nitrogen isotopes generally occurring in nature. In methods wherein it is intended to analyze the breath of the test subject for carbon dioxide hydrolysis product of administered urea, it is particularly preferred to administer isotope-labelled urea to said subject, i.e., carbon-13 or carbon-14 isotope-labelled urea. A preferred method of this invention involves administration of from about 0.1 to about 10 microcuries of C—14 labelled urea.

Breath Analysis

Following the step of administering urea to a human or lower animal subject, the methods of this invention include the step of analyzing the breath of the subject for the presence of hydrolysis products of the administered urea. Accordingly, the specific methods used in the analyzing step of this invention will depend upon the specific hydrolysis product to be detected. Detection of such a hydrolysis product, i.e., carbon dioxide or ammonia, is a positive indication of a gastrointestinal disorder.

A preferred analysis step of this invention employs detection of carbon dioxide. As stated above, in such preferred methods it is particularly preferred to administer isotope-labelled urea to the subject. Isotope-labelled carbon dioxide is then detected as the hydrolysis product, in the breath of the subject. After administration of the isotope-labelled urea, a period of from about 1 to about 180 minutes, preferably from about 10 to about 120 minutes is allowed to elapse. One or more breath samples of the subject are then obtained, as by (for example) use of a ballon which is inflated by the subject. The content of the ballon may be transferred to a storage container for subsequent transport and analysis. One such commercially-available storage container is the Vacutainer®, sold by Becton-Dickenson Company. Prior to use, the Vacutainer is evacuated, i.e., a vacuum created in the container, and it is sealed. The Vacutainer is attached to the ballon by way of a valve, which (when closed) maintains the vacuum in the Vacutainer. Upon opening the valve, some or all of the gaseous content of the ballon is drawn into the Vacutainer. An alternative means for collection of the breath sample(s) is by bubbling the breath through an alkali aqueous solution, thereby collecting carbon dioxide as carbonic acid.

The gaseous breath sample collected from the subject, as described above, is then analyzed for the presence of isotope-labelled carbon dioxide. A variety of methods, among those useful for detection of isotopes in the methods of this invention, is described in G. W. Ewing, *Instrumental Methods of Chemical Analysis,* (4th edition, 1975), incorporated by reference herein. Such methods include, for example, mass spectroscopy. See, P. Klein, et al., "Stable Isotopes and Mass Spectrometry in Nutrition Science" 21 *Analytical Chemistry Symposium Series* 155–166 (1984), incorporated by reference herein. Labelled hydrolysis products can also be detected, for example, by infrared or nuclear magnetic resonance spectroscopy. See, for example, P. Klein, et al., "Application of Stable Isotopies to Pediatric Nutrition and Gastroenterology: Measurement of Nutrient Absorption and Digestion Using $^{13}C$" 4 *Journal of Pediatric Gastroenterology and Nutrition* 9–19 (1985), incorporated by reference herein, and P. Klein, et al., "The Commercial Feasibility of $^{13}C$ Breath Tests" 11 *Analytical Chemistry Symposium Series* 347–352 (1982), incorporated by reference herein. One preferred device for detection of isotope-labelled urea hydrolysis products, useful in the methods of the present invention, is described in the following U.S. Patents, all incorporated by reference herein: U.S. Pat. No. 3,679,899, Dimeff, issued July 25, 1972; U.S. Pat. No. 3,899,252, Dimeff, issued Aug. 12, 1975; and U.S. Pat. No. 4,027,972, Davies, issued June 7, 1977. C-14 labelled carbon dioxide can also be detected as above, or by use of beta-radiation detectors, since the C-14 isotope is radioactive.

The analysis step of this invention may alternatively, or in addition to carbon dioxide detection, employ detection of ammonia from the hydrolysis of administered urea. Such detection of ammonia in the breath of the test subject may be by indirect means, such as by measuring pH changes of the oral or esophageal fluids. An increase in pH reflects the presence of ammonia in the breath, and is a positive indication of a gastrointestianl disease. Detection of ammonia may also be by collection of breath samples, for example as described above. Ammonia in such samples may be detected spectroscopically, or by adsorption onto a pH-sensitive substrate. In one method of this invention, the urea administered to the test subject may be isotope labelled with nitrogen-15 isotope. The N-15 ammonia may then be detected in the breath samples taken from the subjects during the analysis step of this invention.

The following non-limiting example illustrates one method of this invention.

EXAMPLE

In a method according to this invention, a subject presenting symptoms of dyspepsia fasts for approximately eight hours. The subject is then administered a single dose of approximately 3 microcuries of urea, dissolved in water. After approximately 20 minutes, a breath sample is collected from the subject by bubbling the subject's breath through an alkaline aqueous scintillation solution. This solution is then placed in a scintillation counter, and the presence of beta radiation is detected, indicating positively the presence of a gastrointestinal disease in the subject.

What is claimed is:

1. A method for the diagnosis in a human or lower animal subject of a gastrointestinal disorder of the upper gastrointestinal tract caused or mediated by the bacteria *Campylobacter pyloridis,* said method comprising the steps of administering to said subject a safe and effective amount of isotope-labeled urea, and analyzing the breath of said subject for the presence of isotope-labeled carbon dioxide, isotope-labeled ammonia, or both hydrolysis products, wherein the presence of either or both said hydrolysis products is a positive indication of said gstrointestinal disorder in said subject.

2. A method for the diagnosis in a human or lower animal subject of a gastrointestinal disorder of the upper gastrointestinal tract caused or mediated by bacteria which result in the gastric materials of the human or lower animal to contain relatively large quantities of urease, said method comprising the steps of administering to said subject a safe and effective amount of isotope-labeled urea, and analyzing the breath of said subject for the presence of isotope-labeled carbon dioxide, isotope-labeled ammonia, or both hydrolysis products, wherein the presence of either or both said hydrolysis products is a positive indication of said gastrointestinal disorder in said subject.

3. A method for the diagnosis of a gastrointestinal disorder of the upper gastrointestinal tract caused or mediated by bacteria resulting in the gastric materials containing relatively large quantities of urease in a human or lower animal subject, according to claim 2 wherein said analyzing step involves analyzing the breath of said subject for the presence of isotope-labeled carbon dioxide hydrolysis product of said isotope-labeled urea.

4. The method for the diagnosis of a gastrointestinal disorder of the upper gastrointestinal tract caused or mediated by bacteria resulting in the gastric materials containing relatively large quantities of urease in a human or lower animal subject, according to claim 3, wherein said urea is isotope-labeled with carbon-14 isotope.

5. A method for the diagnosis of a gastrointestinal disorder of the upper gastrointestinal tract caused or mediated by bacteria resulting in the gastric materials containing relatively large quantities of urease in a human or lower animal subject, according to claim 3, wherein said urea is isotope-labeled with carbon-13 isotope.

6. A method for the diagnosis of a gastrointestinal disorder of the upper gastrointestinal tract caused or mediated by bacteria resulting in the gastric materials containing relatively large quantities of urease in a human or lower animal subject, according to claim 2, wherein said analyzing step involves analyzing the breath of said subject for the presence of isotope-labeled ammonia hydrolysis product of said isotope-labeled urea.

7. A method for the diagnosis of a gastrointestinal disorder of the upper gastrointestinal tract caused or mediated by bacteria resulting in the gastric materials containing relatively large quantities of urease in a human or lower animal subject, according to claim 6, wherein said urea is isotope-labeled with nitrogen-15 isotope.

* * * * *

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 4,830,010 |
| ISSUED | : | May 16, 1989 |
| INVENTOR(S) | : | Barry J. Marshall |
| PATENT OWNER | : | Barry J. Marshall |

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,260 days from May 16, 2006, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
Commissioner of Patents and Trademarks